United States Patent
Capaldi et al.

(10) Patent No.: US 11,478,497 B2
(45) Date of Patent: Oct. 25, 2022

(54) METHODS AND COMPOSITIONS FOR TREATING EUKARYOTIC INFECTIONS VIA ALTERING AGGREGATION DYNAMICS OF RAPTOR/KOG1

(71) Applicant: Arizona Board of Regents on Behalf of The University of Arizona, Tucson, AZ (US)

(72) Inventors: Andrew P. Capaldi, Tucson, AZ (US); James E. Hughes Hallett, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 215 days.

(21) Appl. No.: 15/535,019

(22) PCT Filed: Dec. 18, 2015

(86) PCT No.: PCT/US2015/066833
§ 371 (c)(1),
(2) Date: Jun. 9, 2017

(87) PCT Pub. No.: WO2016/100893
PCT Pub. Date: Jun. 23, 2016

(65) Prior Publication Data
US 2017/0360820 A1    Dec. 21, 2017

Related U.S. Application Data

(60) Provisional application No. 62/093,590, filed on Dec. 18, 2014.

(51) Int. Cl.
| | | |
|---|---|---|
| A61K 39/395 | (2006.01) | |
| A61K 31/7056 | (2006.01) | |
| A61K 31/155 | (2006.01) | |
| A61K 31/60 | (2006.01) | |
| A61K 45/06 | (2006.01) | |
| C07K 16/18 | (2006.01) | |

(52) U.S. Cl.
CPC ........ *A61K 31/7056* (2013.01); *A61K 31/155* (2013.01); *A61K 31/60* (2013.01); *A61K 39/3955* (2013.01); *A61K 45/06* (2013.01); *C07K 16/18* (2013.01); *C07K 2317/76* (2013.01); *G01N 2500/10* (2013.01); *Y02A 50/30* (2018.01)

(58) Field of Classification Search
None
See application file for complete search history.

(56) References Cited

U.S. PATENT DOCUMENTS

| 8,486,643 B2 | 7/2013 | Sabatini et al. | |
| 2014/0206016 A1* | 7/2014 | Lozano | C12Q 1/04 435/7.1 |
| 2014/0364595 A1* | 12/2014 | Bapat | A61K 8/37 536/17.4 |

FOREIGN PATENT DOCUMENTS

WO   WO 2014052640 A1   4/2014

OTHER PUBLICATIONS

Roeleveld-Versteegh et al. Ned Tijdschr. Gebeeskd 142: 2256-2258, 1998.*
Al-Saif et al. J. Thermal. Anal. Calorim. 111: 2079-2096, Online pub May 6, 2012.*
Olar et al. Eur. J. Medicinal Chem. 45: 2868-2875, Mar. 17, 2010.*
Cheng et al. Science 345: pp. 1-18, 2014.*
Shirazi et al. PLOS ONE 9: e108635, pp. 1-9, 2014.*
New Riverside University Dictionary, The Riverside Publishing Company, p. 933, 1984.*
Illustrated Stedman's Medical Dictionary, 24th Edition, Williams and Wilkins, London, p. 707, 1982.*
Bastidas et al. The Enzymes 27: 199-227, Chapter 11, 2010.*
(Gwinn, DM et al.) AMPK Phosphorylation of Raptor Mediates a Metabolic Checkpoint. Molecular Cell. Apr. 25, 2008, vol. 30, pp. 214-226; abstract; p. 219, first column, second paragraph—second column, first paragraph; figures 2, 6, 7. 001: 10.1 016/j.molcel.2008. 03.003.
(Takahara, T et al.) Transient Sequestration ofTORC1 into Stress Granules during Heat Stress. Molecular Cell. Jul. 27, 2012, vol. 47, pp. 242-252; Figure 3; 001: 10.1016/j.molcel.2012.05.019.
(Lam, KKY et al.) Nitazoxanide Stimulates Autophagy and Inhibits mTORC1 Signaling and Intracellular Proliferation of *Mycobacterium tuberculosis*. PLoS Pathogens. May 10, 2012, vol. 8 No. 5: e1002691, pp. 1-15; p. 9, first column, fourth paragraph. DOI:10.1371/journal. ppat.1002691.
(Hallet, Jeh et al.) State Transitions in the TORC1 Signaling Pathway and Information Processing in *Saccharomyces cerevisiae*. Genetics. Oct. 2014, vol. 198, pp. 773-786; entire document. 001: 10.1534/genetics.114.168369.

(Continued)

*Primary Examiner* — Jana A Hines
*Assistant Examiner* — Khatol S Shahnan Shah
(74) *Attorney, Agent, or Firm* — Nguyen Tarbet LLC

(57) ABSTRACT

Methods and compositions for activating TORC1 aggregate formation in a fungi or a parasite, wherein TORC1 aggregate formation inhibits growth of the fungi or parasite. TORC1 aggregate formation may be activated using small molecules or other agents, and said agents may be used to treat or prevent a disease or condition associated with the fungi and parasite. The agent may target Kog1 of TORC1, e.g., the agent may directly or indirectly inhibit Kog1 leading to aggregation of the TORC1 complex.

4 Claims, 10 Drawing Sheets
(5 of 10 Drawing Sheet(s) Filed in Color)

Specification includes a Sequence Listing.

(56) References Cited

OTHER PUBLICATIONS (Hallet, Jeh et al.) Snf1/AMPK Promotes the Formation of Kog1/Raptor-bodies to Encrease the Activation Threshold ofTORC1 in Budding Yeast. eLife. Oct. 6, 2015, vol. 4: e09181; pp. 1-19; entire document. 001: 10.7554/eLife.09181.

Roberto Zoncu et al., mTOR: from growth signal integration to cancer, diabetes and ageing, Nature Reviews, Molecular Call Biology, Jan. 2011, vol. 12.

* cited by examiner

500 - LQSRKSISLQ SSQQQLQQQQ QQQQQFTGFF EQNLTAFELW - 540  . . .  830 - QLHSQLQHLQ NQSHLQQQQS QQQQQHLEQQ QMKIEKQIRH - 870

500 - LQSRKSISLQ SSAAALAAAA AAAAAFTGFF EQNLTAFELW - 540  . . .  830 - QLHSQLQHLQ NQSHLAAAAS AAAAHLEQQ QMKIEKQIRH - 870

Overall description of changes in TORC1:

- Distribution of Kog1-bodies in wild-type (WT) cells following acute glucose starvation:

- Frequency distribution of Kog1-bodies in WT cells following acute glucose starvation:

Mean = 1.40/cell with foci

- Distribution of Kog1-bodies in WT cells following natural/chronic glucose starvation:

| Strain | Time point (hrs) | Mean (%) | SD (%) |
|---|---|---|---|
| WT | 24 | 87.4 | 6.7 |

- Kog1-body formation in additional stress/starvation conditions (acute) in WT cells:

SD = 2% glucose
-N2 = nitrogen (and amino acid) starvation
-G = glucose starvation (from 1st figure)
-NG = nitrogen and glucose starvation
+KCl = osmotic stress

- Distribution of Kog1-bodies in mutant cells following acute glucose starvation

- Kog1 distribution/localization is distinct from Tor1 following acute glucose starvation:

Kog1-YFP 0% glucose 30min localization to:
body = 57%

Tor1 GFP 0% glucose 30min localization to:
body = 21%
vacuole = 27%
neither = 52%

What do Kog1 foci do?

- Kog1 foci formation affects TORC1 signaling. Sch9-HA bandshifts (measure TORC1 activity) following glucose repletion:

* Kog1 body plays a role in cell survival during long term starvation:

Cell survival after 10 days.

173 = WT
844 = Glutamine mutant 1
871 = S491/4A

Cell survival after 7 days.

173 = WT
844 = Glutamine mutant 1

METHODS AND COMPOSITIONS FOR TREATING EUKARYOTIC INFECTIONS VIA ALTERING AGGREGATION DYNAMICS OF RAPTOR/KOG1

CROSS REFERENCE

This application is a 371 application and claims benefit of International Patent Application No. PCT/US15/66833 filed Dec. 18, 2015, which claims benefit of U.S. Provisional Patent Application No. 62/093,590 filed on Dec. 18, 2014, the specification(s) of which is/are incorporated herein in their entirety by reference.

GOVERNMENT SUPPORT

This invention was made with government support under Grant No. R01 GM097329 awarded by NIH. The government has certain rights in the invention.

FIELD OF THE INVENTION

The present invention relates to systems, methods, and compositions for treating or preventing diseases associated with eukaryotic organisms, more particularly to methods and compositions for directly or indirectly triggering and/or permitting, or inhibiting Raptor/Kog1 aggregation in specific eukaryotes.

BACKGROUND OF THE INVENTION

TOR Pathway

The TOR Kinase (known as "mTOR" in mammals), as part of TOR Complex I (TORC1; or mTORC1 in mammals) controls cell growth and metabolism in all eukaryotes (See FIG. 1). When nutrient and growth factor levels are high, the TOR kinase is active, and drives growth by promoting anabolic processes such as protein synthesis and by inhibiting catabolic processes, such as autophagy. In contrast, when nutrient or growth factor levels are low, or cells are exposed to stress, TOR signaling is inhibited. As a result, mass accumulation is limited and catabolic and stress response pathways are up-regulated. If strong TOR inhibition persists, cells enter a quiescent state.

Growth regulation by the TOR kinase depends on its participation in the multi-protein complex TORC1 (FIG. 1a). Once activated, TORC1 affects cell growth through numerous downstream regulators. In *S. cerevisiae*, where TOR output is best understood, TORC1 acts on, and through, two well characterized effectors: (1) Sch9, an S6 kinase that coordinates protein synthesis through regulation of RNA polymerases I and III, ribosome synthesis and biogenesis, and protein translation and (2) TAP42, a regulatory subunit of protein phosphatase 2A (PP2A), that controls metabolic and stress responses (FIG. 1b). TORC1 also acts through Sfp1, a transcription factor that regulates ribosome synthesis, and the kinase Yak1 (FIG. 1b). The overall structure, and the molecular makeup of TORC1 and the TOR pathway are similar in humans and other eukaryotes.

TORC1 Regulation

Progress has been made towards identifying the pathways and mechanisms underlying TORC1 regulation. It has been shown that the TSC1 and 2 tumor suppressor proteins (which are absent in yeast) act to transmit signals from insulin, epidermal growth factor (EGF), AMP dependent kinase (AMPK), and other pathways, to TORC1. More recently, it was found that AMPK also regulates TORC1 activity independently of TSC1/2, by phosphorylating Kog1/Raptor (FIG. 1a) directly at two sites, one of which is conserved across eukaryotes. This activity ensures that cell growth is limited as cellular energy levels wane. Finally, a family of Ras related GTP binding proteins (Rag proteins) have been found to regulate TOR activity in response to amino acid availability, through direct binding to TORC1, in both yeast and human cells.

Stress also influences TOR pathway activity, although it is unclear whether this is due to direct regulation of TORC1 or regulation of one or a few downstream components of the TOR pathway. The pathways involved in stress dependent TOR regulation are also unknown. In human cells, it has been shown that osmotic stress leads to a rapid decrease in phosphorylation of S6 kinase 1 (S6K1) and 4EBP-1, resulting in reduced protein translation. These affects are independent of TSC1/2 and thus the underlying mechanism may be conserved in yeast. Down regulation of S6K1 activity has also been found in human cells in mechanical, ultraviolet radiation, and heat stress. In *S. cerevisiae*, similar effects have been seen. Most strikingly, osmotic, heat, and oxidative stress trigger a rapid decrease in Sch9 (the yeast S6K1) phosphorylation at the TORC1 target sites. These same stresses also cause the TORC1 regulated transcription factor Sfp1 to be exported from the nucleus.

TOR Pathway Regulation in Salt Stress

Previous studies of TOR pathway signaling in stress have been limited to measuring phosphorylation of a single substrate, Sch9. As a result it was not clear whether stress signals inhibit TORC1 activity directly or simply act on one or two TORC1 targets proteins. To help distinguish between these possibilities, the complete output of TORC1 pathway in osmotic stress was measured using DNA microarrays. To do this, the cellular response was monitored with and without the potent TORC1 inhibitor rapamycin in 0.4M KCl and three control conditions: amino acid starvation, nitrogen starvation and log growth conditions. As shown in FIG. 2, rapamycin treatment of rapidly growing cells, where TORC1 is active, led to widespread and dramatic reprogramming of gene expression (FIG. 2a). However, in KCl stress and starvation conditions, rapamycin had almost no influence on gene expression (FIG. 2a). These results suggest that TORC1 is inhibited in stress (as shown previously in starvation conditions) so that rapamycin has no additional effect.

Consistent with the hypothesis that TORC1 activity is inhibited in stress, genes involved in ribosome synthesis, biogenesis and tRNA synthesis are down-regulated in KCl to a level at or near that found in rapamycin (FIG. 2a, columns 1 and 5). This is not just due to down-regulation of Sch9 activity (which does occur, FIG. 2b) as blocking the activity or regulation of this kinase has a relatively small effect on ribosome protein and biogenesis gene expression (2-fold versus>20-fold in KCl stress). Thus, it could be concluded that TORC1 stops phosphorylating and activating all (or most) of the regulators in the Sch9 branch (blue/purple, FIG. 1b) of the TOR pathway (Sch9, Sfp1, Yak1 and likely others) in stress.

It was also found that the output of TORC1 pathway is different in salt stress than in rapamycin. Specifically, while both stimuli cause down-regulation of ribosome genes, only rapamycin triggers activation of the carbonic acid, amino acid and nitrogen metabolic pathways (FIG. 2a). These metabolic pathways are targets of TORC1 via TAP42/PP2A and the transcription factors Gat1, Gln3, Rtg1/3 (FIG. 1b). This data shows that salt stress inhibits growth by blocking activation of the Sch9 branch of the TOR pathway, but does not trigger TORC1 dependent reprogramming of metabolism through PP2A. This metabolic reprogramming is also known to occur due to TORC1 inhibition in starvation conditions. Therefore, these results suggest that the output of the TOR pathway is stimuli specific. This has important implications for future studies examining the role TOR pathway in cell growth and metabolism and in drug development.

An interpretation of the microarray data is that stress alters the conformation of TORC1 such that phosporylation of the Sch9 branch of the pathway, but not Tap42-PP2A, is blocked and the allosteric inhibitor rapamycin-Fpr1 (rapamycin-Fkb12 in mammals) can no longer bind/repress TORC1. Alternatively, TORC1 activity may be completely inhibited in stress, so that addition of rapamycin has no further effect, but an additional modification to the Tap42/PP2A complex keeps it from being activated by dephosphorylation at the TORC1 target sites. Models that do not include direct regulation of TORC1 in stress are also possible, but they may have to invoke a stress specific modification to the Tap42-PP2A branch of the pathway that has no affect on gene expression (as these genes are not regulated by stress) but blocks activation of the pathway by rapamycin.

In osmotic stress, Hog1/p38, the terminal kinase in the HOG pathway, is known to regulate many aspects of the stress response including transcription, chromatin remodeling, cell cycle check-points, and ion and glycerol channel regulation. Therefore, it was tested whether Hog1/p38 plays a role transmitting stress signals to TORC1 by comparing expression in hog1Δ and wild-type cells both with and without rapamycin (e.g., with and without TORC1 activity) using DNA microarrays. These analyses revealed that Hog1 does in fact repress TORC1 in salt stress conditions. This repression is manifest as approximately 3-fold less ribosome gene repression in hog1Δ than wild-type cells in 0.4M KCl (FIG. 2c, column 5). The hog1Δ strain is also far more sensitive to rapamycin in salt stress that the wild-type strain (4 fold more repression in hog1Δ than wt, FIG. 2c), indicating that TORC1 is partially active in stress in the absence of Hog1.

TOR pathway activity was measured in the hog1Δ strain by following TORC1 dependent phosphorylation of Sch9 (FIG. 2d). Consistent with the microarray results, 40% more phosphorylation was found at the six TORC1 dependent C-terminal sites (after 10 min) in KCl stress when Hog1 is deleted (FIG. 2d).

Together, this data shows that the MAPK Hog1/p38, plays a role in repressing TORC1 signaling through Sch9, and possibly other regulators in the Sch9 branch of the pathway, in salt stress conditions.

TORC1 and Kog1

It was recently discovered that glucose and energy control the total amount of TORC1 activity in each cell in budding yeast (see Hughes Hallett, Luo, and Capaldi, 2014, the disclosure of which is incorporated in its entirety herein by reference). Glucose and energy levels control TORC1 activity via AMP activated protein kinase (AMPK or Snf1). When adequate energy levels are present, Snf1/AMPK is inactive and TORC1 is localized to the vacuolar (lysosomal) membrane, where it interacts with activator proteins such as the Rags and Rho1. Under stress, e.g., when glucose/energy levels fall, Snf1/AMPK is activated, leading to TORC1 inhibition.

When this happens, the key regulatory component of TORC1, known as Kog1 in yeast (Raptor in humans), relocalizes and aggregates in each cell (see FIG. 3a). Examination of the Kog1 peptide sequence revealed two glutamine repeat sequences. Glutamine rich sequences are predicted to drive assembly of the protein into a prion-like aggregate (see FIG. 4). Mutating either glutamine repeat region reduces the formation of the aggregates (Kog1 bodies) (see FIG. 3b). Mutants that cannot form Kog1 bodies activate the TORC1 complex following starvation more quickly than wild type cells (see FIG. 5). In other words, sequestration of Kog1 bodies helps cells remain in a state with TORC1/Sch9 inhibited until the cell experiences ideal conditions for an extend time. Without the Kog1 bodies, TORC1 is immediately activated even after long periods of starvation; this makes the cell more susceptible to stress (including drug treatment) and subsequent starvation.

Alternatively, mutants or drug treatments driving the aggregation of Kog1 would inhibit the growth and replication of these cells via inhibition of the TORC1 pathway.

Examination of Kog1/Raptor in other organisms reveals that many microbes, including pathogenic fungi and worms, e.g., parasites, also have glutamine repeats, suggesting that formation of Kog1 aggregates is a common strategy used to survive long-term stress and starvation. However, the mammalian and plant forms of Kog1 (i.e., Raptor) do not contain glutamine repeats or prion-like domains. Therefore compositions, agents, or drugs that either block or trigger/permit Kog1 aggregation may help fight infections in humans, animals, and plants.

A model using a tagged Kog1 (e.g., Kog1-YFP (Yellow Fluorescent Protein) (e.g., YFP-tagged Kog1) or other appropriate tags, e.g., green fluorescent protein, red fluorescent protein, quantum dots, immunohistochemistry agents, etc.) may be used to screen for these drugs. In addition, other genetic regulators or other components involved in the pathways may be discovered, which may provide additional targets for drugs.

SUMMARY OF THE INVENTION

The present invention features methods (and compositions) for inhibiting fungal or parasitic survival or replication (e.g., in an animal, plant, in vitro, etc.) in a subject in need thereof. In some embodiments, the method comprises introducing to a cell, an animal, or a plant an agent that activates TORC1 aggregate formation, wherein the TORC1 aggregate formation inhibits growth of the fungi or parasite. In some embodiments, the subject has been identified as having a condition associated with a fungi or parasite.

The present invention also features methods (and compositions) for treating or preventing a disease or a condition associated with a fungi or a parasite. In some embodiments, the method comprising administering to a subject (in need thereof) an agent that activates TORC1 aggregate formation, wherein the TORC1 aggregate formation inhibits growth of the fungi or parasite. In some embodiments, the subject includes a human, an animal, or a plant. In some embodiments, the subject has been identified as having a disease or condition associated with a fungi or parasite.

In some embodiments, the agent that activates TORC1 aggregate formation targets Kog1 of TORC1. In some embodiments, the agent binds to Kog1. In some embodiments, the agent inhibits Kog1 indirectly. In some embodiments, the disease or condition associated with the fungi or the parasites is parasitic worms, malaria, leishmaniasis, giardia infection, or a candidiasis infection.

In some embodiments, the agent comprises a small molecule. In some embodiments, the small molecule comprises metformin, PT 1, salicylsalicylic acid, Phenformin, AICAR, A-769662, Acadesine, orsomorphin, 1,1-Dimethylbiguanide hydrochloride, or BML-275. In some embodiments, the agent comprises an antibody or a fragment thereof. In some embodiments, the antibody or fragment thereof is monoclonal or polyclonal, nanobody. In some embodiments, the parasite is selected from the group consisting of Helminths, *Plasmodium, Leishmania*, and *Giardia*.

In some embodiments, the method further comprises co-treating the subject with an antifungal drug or an antiparasitic drug.

The present invention also features methods for screening in vitro for a compound that activates TORC1 aggregate formation. In some embodiments, the method comprises introducing a test compound to a first cell system and a second cell system, the first cell system comprising test cells expressing Kog1 labeled with a tag, the second cell system comprising control cells expressing Kog1 labeled with a tag; subjecting the cell systems to a stress; visualizing the tags of the cell systems; and calculating the amount of Kog1 aggregates formed in the cell systems by calculating the number of foci of the tags, wherein if the amount of Kog1 aggregates formed is more in the first cell system than in the second cell system, the compound activates TORC1 aggregate formation. In some embodiments, the tag comprises a fluorescent protein. In some embodiments, the tag comprises YFP, GFP, or RFP. In some embodiments, the stress comprises glucose starvation.

See also Hughes Hallet et al., Snf1/AMPK promotes the formation of Kog1/Raptor-bodies to increase the activation threshold of TORC1 in budding yeast (2015) Elife 6:4, the disclosure of which is incorporated herein in its entirety.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

DETAILED DESCRIPTION OF THE INVENTION

Figure 1:
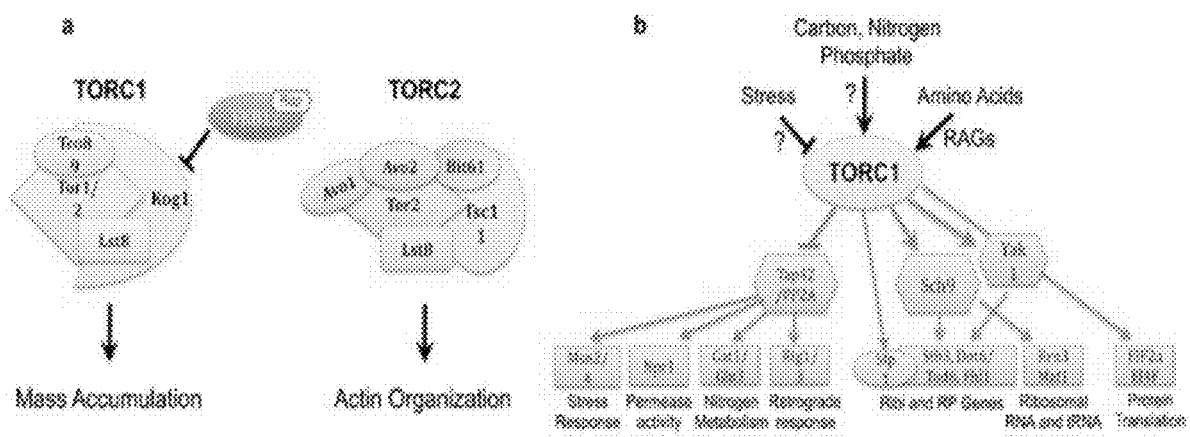
FIG. 1 shows the TOR pathway in budding yeast. (a) The activity of the TOR kinase (Tor1 and 2) depends on its participation in one of two protein complexes (TORC1 and TORC2). Only TORC1 activity is repressed by the small molecule rapamycin and this inhibition depends on an interaction with the prolyl isomerase Fpr1/Fkb12. The proteins in TORC1 and TORC2, except Tco89, are conserved across the eukaryotes. (b) TORC1 is regulated, in response to stress and a range of nutrients, through unknown pathways and mechanisms. Amino acids act on TOR through the RAG GTPases. When activated, TORC1 up-regulates growth through a variety of mechanisms (blue genes), and down regulates anabolic metabolism via TAP42/PP2A, stress genes (organge genes) and autophagy (not shown). Hexagons-kinases and phosphates: squares-transcription factors (TF): circle the directly regulated TF Sfp1.
Figure 2:
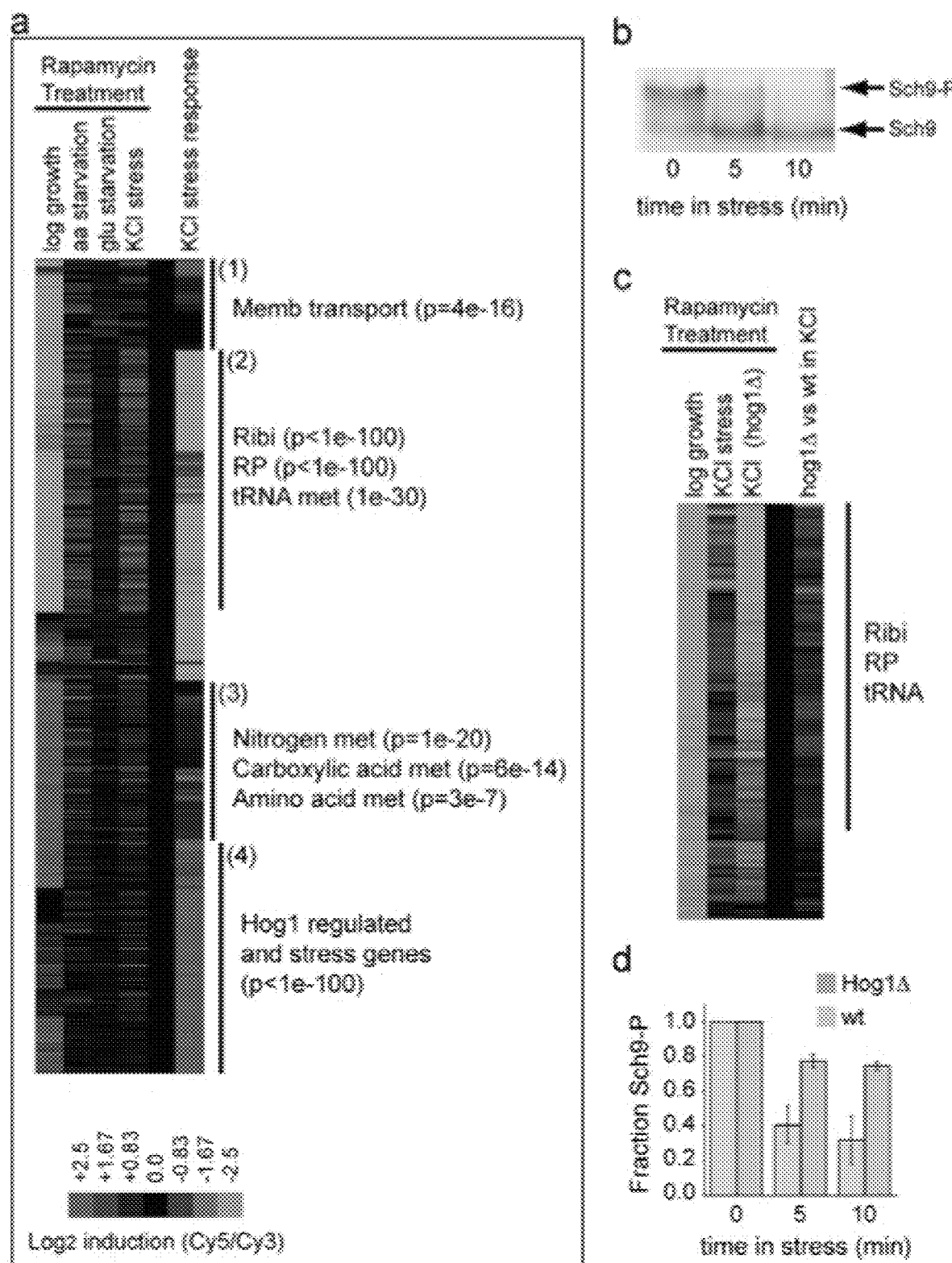
FIG. 2 shows TORC1 regulation in KCl stress. (a) DNA microarray data comparing the gene expression program activated by KCl stress and the TORC1 inhibitor rapamycin. The rapamycin experiments compare the mRNA levels from cells grown in the conditions indicated on the diagram prior to, and 20 minutes after, treatment with 200 ng/ml rapamycin (aa=amino acid, glu=glucose). The KCl stress experiment compares the mRNA levels from cells in log growth conditions (YEPD, OD=0.6) prior to, and 20 min after, treatment with 0.4M KCl. In all of these experiments cDNA from cells treated with a stimuli are labeled with Cy5 while untreated cells are labeled with Cy3. Thus, genes activated by KCl or rapamycin are red on the heat map while genes repressed in these stimuli are green. The heat map shows data for all 700 genes that are up- or down-regulated >4-fold in one of the experiments. Four major gene sets were found by clustering; (1) genes down-regulated in rapamycin but not KCl, (2) genes down-regulated in both KCl and rapamycin, (3) genes activated in rapamycin but not KCl, and (4) genes activated primarily in KCl stress. The major ontology groups for each set are listed, along with their statistical significance. Experiments were performed using Agilent 60-mer oligonucleotide arrays, and were repeated at least two-times. (b) Sch9 is dephosphorylated in KCl stress. A phosphorylation-induced shift in the electrophoretic mobility of Sch9-3HA was measured by performing a western blot to a SDS-PAGE gel loaded with extract from cells collected before and after treatment with 0.4M KCl, using an anti-HA antibody. To increase the magnitude of the band shift for this large protein (110 kDa with tag), and ensure that we measure phosphorylation at the 6 C-terminal TORC1 target sites, proteins in the extract were cut into fragments using 2-Nitro-5-thiocyanatobenzoic acid, prior to loading on the gel. The image shows the smallest detected fragment, approximately 50 kDa (⅓ of protein without tag). Previous experiments identified the shift in this fragment and showed that it is due to dephosphorylation of Sch9 at the TORC1 sites. (c) Hog1/p38 inhibits TORC1 activity in KCl stress. The expression data for genes repressed more than 4-fold by rapamycin treatment in the log growth and KCl stress experiments from (a) are shown together with data from arrays comparing mRNA from 1) hog1Δ cells in KCl and rapamycin for 20 min (Cy5) to hog1Δ cells in KCl alone for 20 min (Cy3) and 2) hog1Δ in 0.4M KCl for 20 min (Cy5) to wt cells in the same conditions (Cy3). (d) Sch9 dephosphorylation in stress is partially blocked by deletion of Hog1. The experiment described in (b) was carried out in triplicate in wild-type and hog1Δ strains and the fraction of protein in the phosphorylated state was quantified using densitometry. The fraction of Sch9 phosphorylated at each time-point was normalized using the data at time 0 to eliminate noise from to prep-to-prep variation in the total level of Sch9 phosphorylation (which varied from 80 to 90%, at time=0, in hog1Δ and wt cells). The graph shows the average and standard deviation of each time-point from the three normalized data sets.
Figure 3:
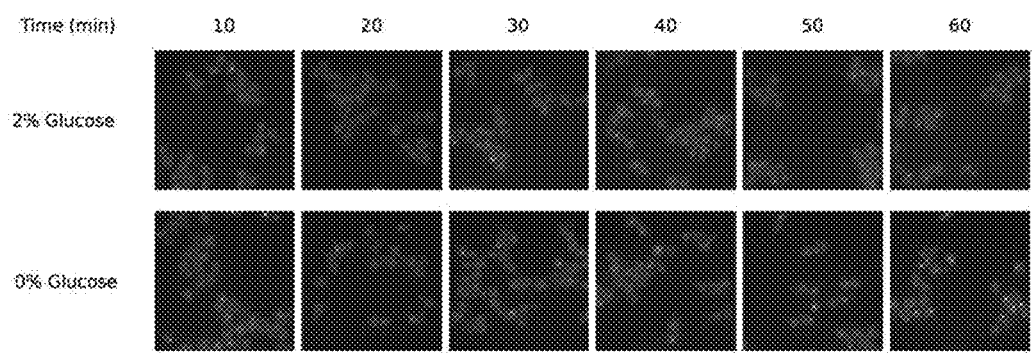
FIG. 3 shows Kog1 aggregation in glucose starvation. (a) Images of Kog1-YFP cells grown in synthetic medium with 2% glucose (SD medium, top row), or grown in SD medium and transferred to synthetic medium without glucose (bottom row) taken at 60× magnification on an inverted fluorescence microscope. The fraction of cells with a Kog1 aggregate at each time point are shown in the graph below. Each point shows the average and standard deviation from at least three separate experiments. (b) The formation of Kog1-YFP aggregates is inhibited strongly in cells missing the AMP activated protein kinase AMPK/Snf1 and in cells where a stretch of glutamine repeats has been replaced by alanine (see FIG. 2 for details).
Figure 3:
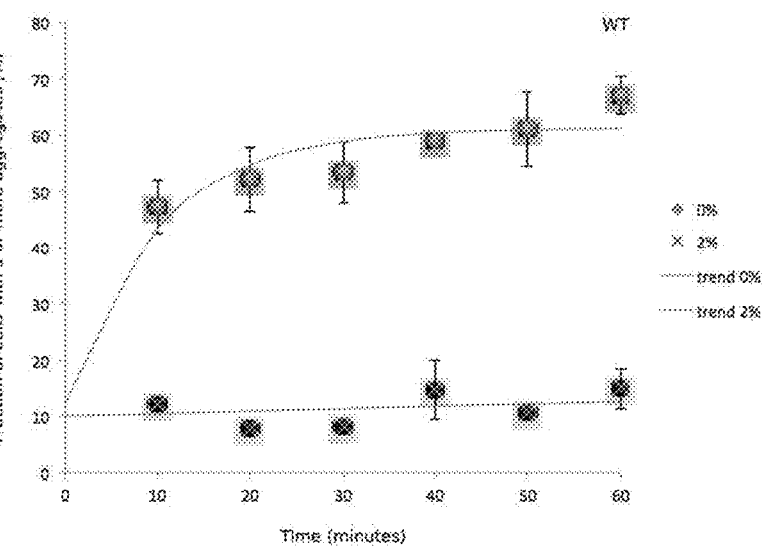
Figure 3:
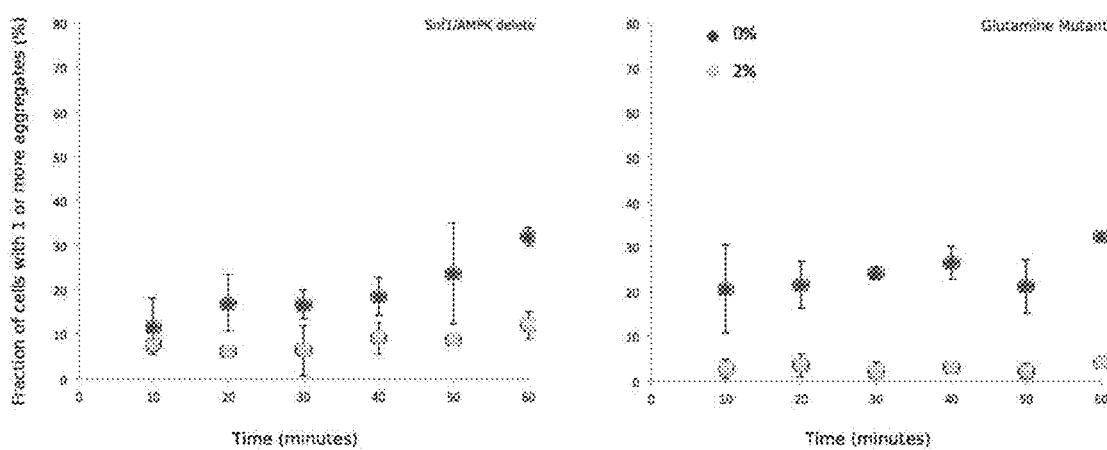
Figures 4, 5:
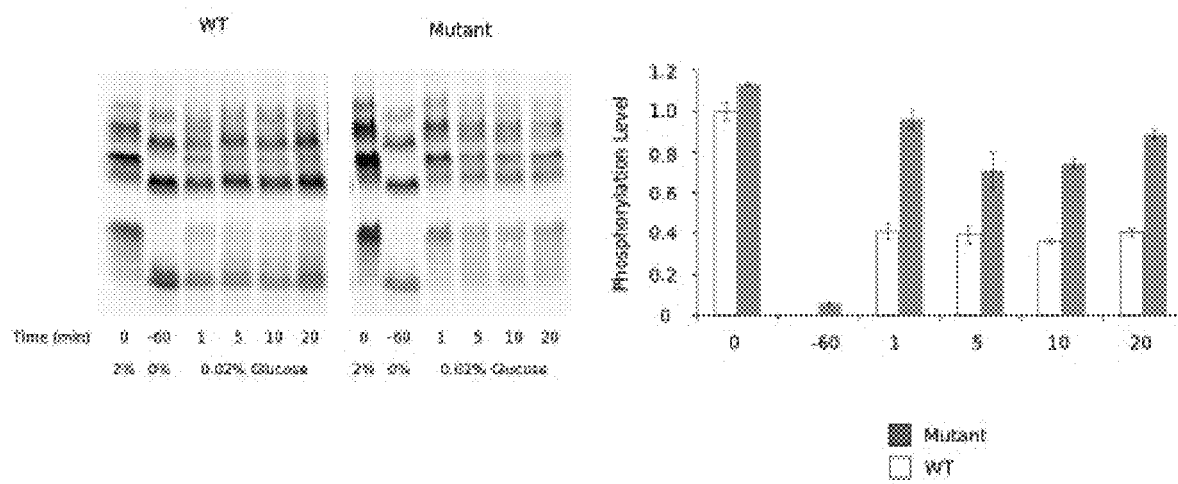
FIG. 4 shows Kog1 contains two glutamine repeat regions, similar to those found in prion proteins (see the top sequence of FIG. 4 showing LQSRKSIS- LQSSQQQLQQQQQQQQQFTGFFEQNLTAFELW (SEQ ID NO: 1) and QLHSQLQHLQNQSHLQQQQSQQQQQ-HLEQQQMKIEKQIRH (SEQ ID NO: 2)). To probe the function of these regions, the core of these repeats was replaced with stretches of alanine (see bottom sequence of FIG. 4 showing LQSRKSISLQSSAAALAAAAAAAAF-TGFFEQNLTAFELW (SEQ ID NO:3) and QLHSQLQH-LQNQSHLAAAASAAAAQHLEQQQMKIEKQIRH (SEQ ID NO:4)).
FIG. 5 shows TOR kinase activity is inhibited by Kog1 aggregation. To measure TORC1 activity the phosphorylation of the s6 kinase, Sch9, was followed using a bandshift assay (as described in Hughes Hallet et al., 2014). To perform this assay cells carrying Sch9 with an HA epitope tag at the C-terminus were grown in synthetic medium containing 2% glucose, and then transferred to synthetic medium containing either 0% or 0.02% glucose, as indicated on the gel (left hand images). The proteins in the cell were then precipitated using trichloroacetic acid, the cells lysed, and the protein extracted by bead beating in urea buffer. Proteins were then cut into fragments using 2-nitro-5-thio-cyanatobenzoic acid (NTCB), and Sch9 detected by SDS-PAGE and western blotting using an anti-HA antibody. The 6 TORC1 phosphorylation sites in Sch9 are all located in the C-terminus of the protein and thus the lowest bands on the gel show changes in Sch9 phosphorylation at these sites (as the HA tag is also at the C-terminus). Examining phosphorylation in the wild-type (left gel) and glutamine mutant Kog1 (right gel) it is seen that Sch9 is fully phosphorylated in 2% glucose (upper band/arrow), and fully dephosphorylated after 60 min in 0% glucose (lower band/arrow). However, once cells starved for glucose are exposed to low concentrations of glucose, the two strains behave differently (see quantitation graphs on the right). In the wild-type strain, 0.02% glucose triggers phosphorylation of approximately 40% of the Sch9 in the population. This matches the fraction of the cells that do not have a Kog1 aggregate in glucose starvation conditions. In contrast, we see that 90-100% of the Sch9 is activated in cells with mutated glutamine repeats. Thus, cells with Kog1 aggregates are unable to activate TORC-Sch9 and grown in low concentrations of glucose. Nearly identical results are seen in 0.1% glucose.
Figure 6:
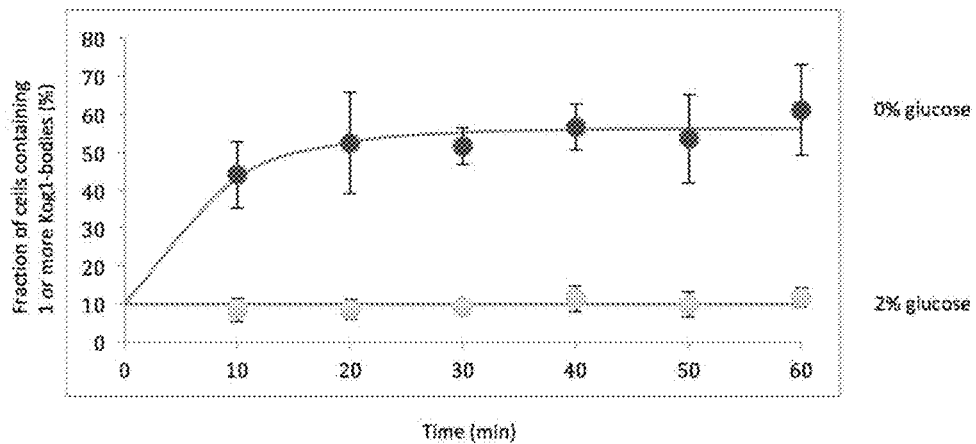
FIG. 6 shows the distribution of Kog1 bodies in WT cells following acute glucose starvation (top) and the frequency distribution of Kog1 bodies in WT cells following acute glucose starvation (middle). The bottom panel shows the distribution of Kog1 bodies in WT cells following natural/chronic glucose starvation.
Figure 6:
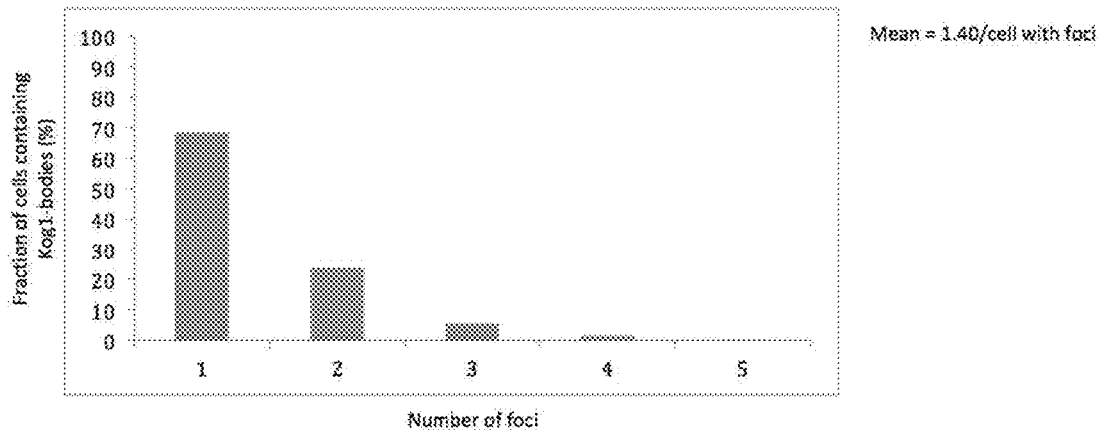
Figure 7:
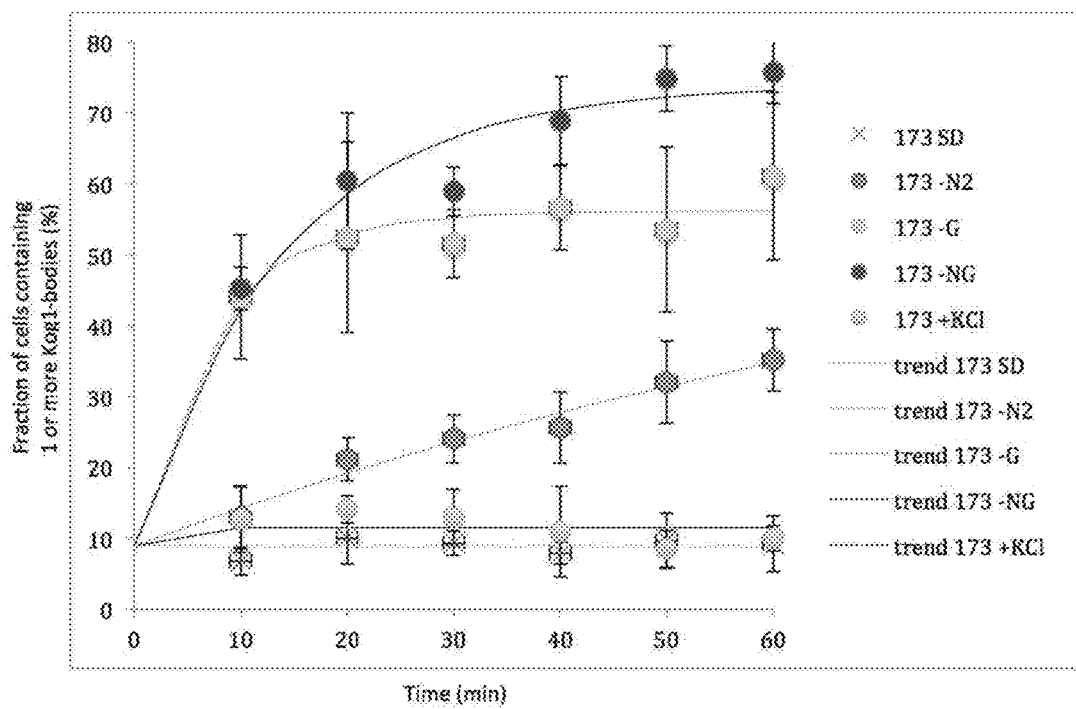
FIG. 7 shows Kog1 body formation in additional stress/starvation conditions (acute) in WT cells (top), and the distribution of Kog1 bodies in mutant cells following acute glucose starvation (bottom).
Figure 7:
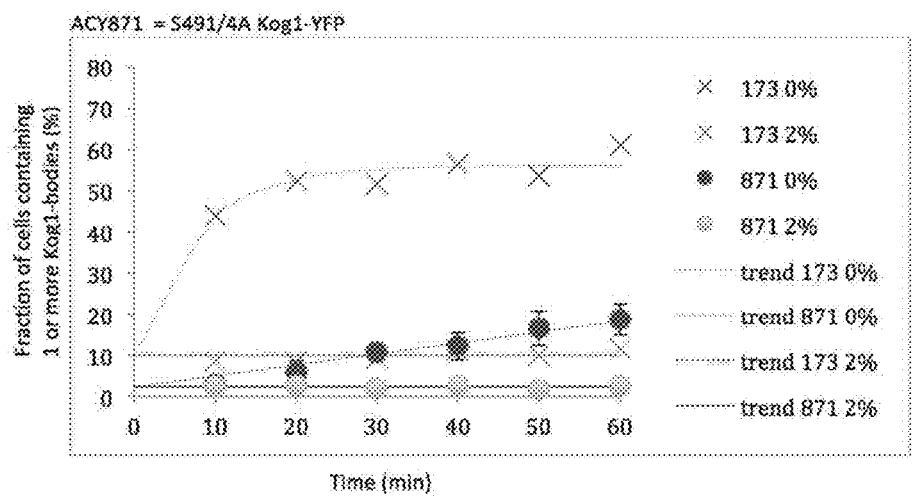
Figure 8:
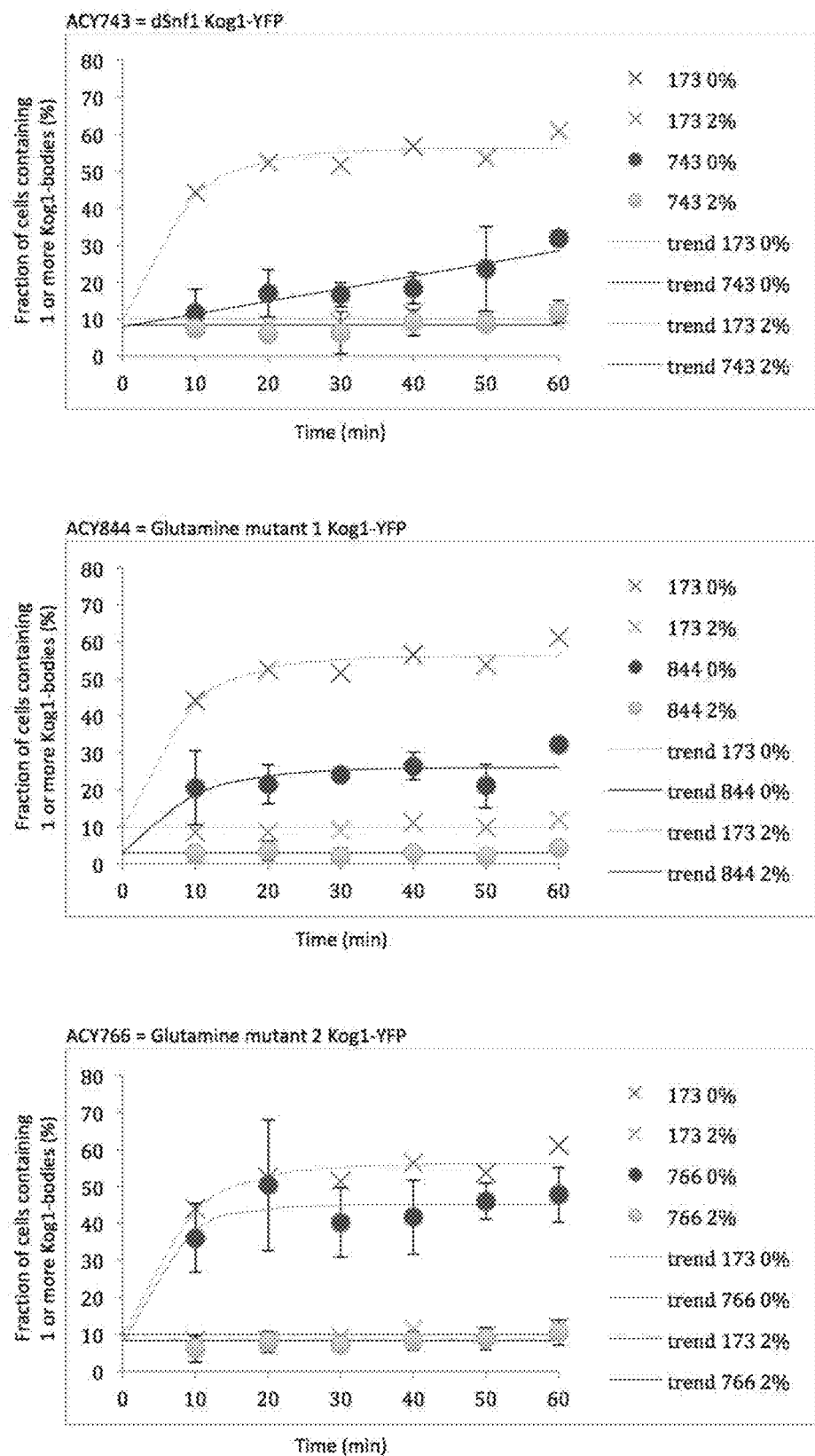
FIG. 8 compares the fraction of cells containing 1 or more Kog1 bodies in various strains.
Figure 9:
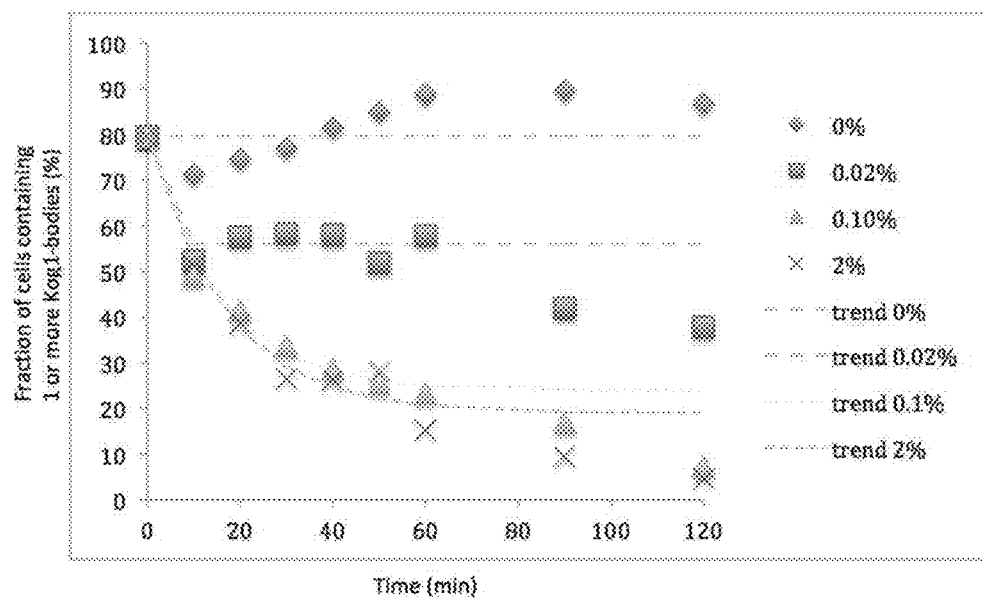
FIG. 9 shows the dynamics of Kog1 foci (Kog1 bodies) resolution following glucose repletion in WT cells (top). The bottom panels show that cycloheximide (CHX) alone (a TORC1 activator) does not trigger disaggregation of Kog1.
Figure 9:
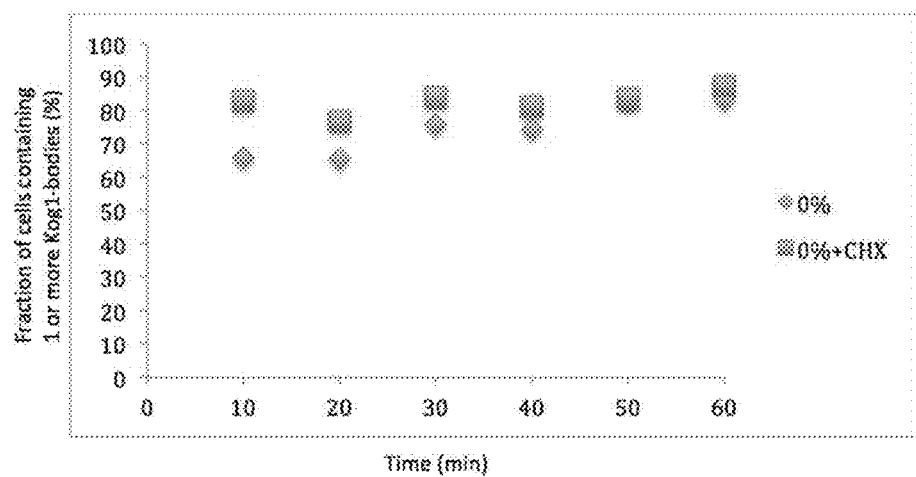
Figure 10:
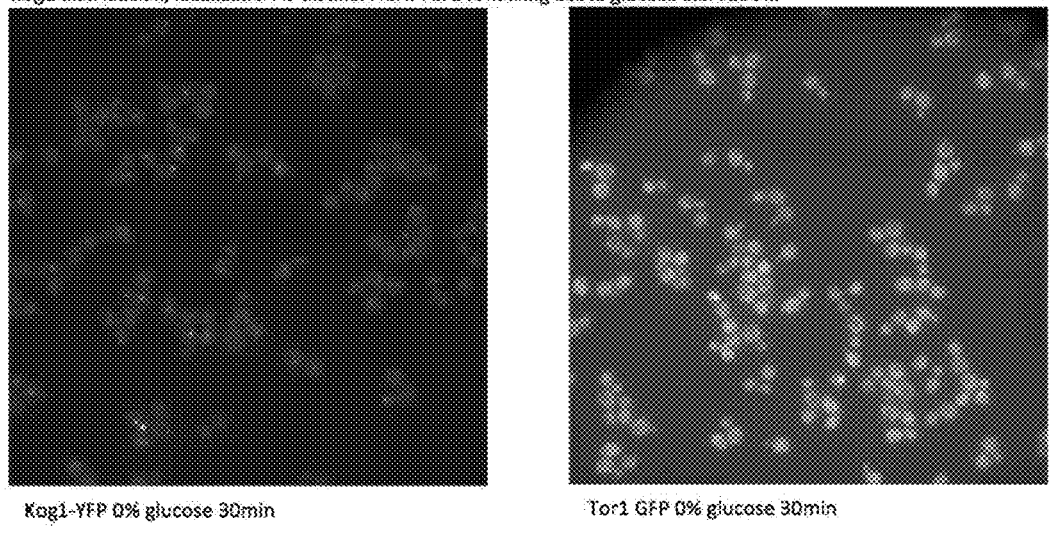
FIG. 10 shows that Kog1 distribution/localization is distinct from Tor1 following acute glucose starvation.
Figure 11:
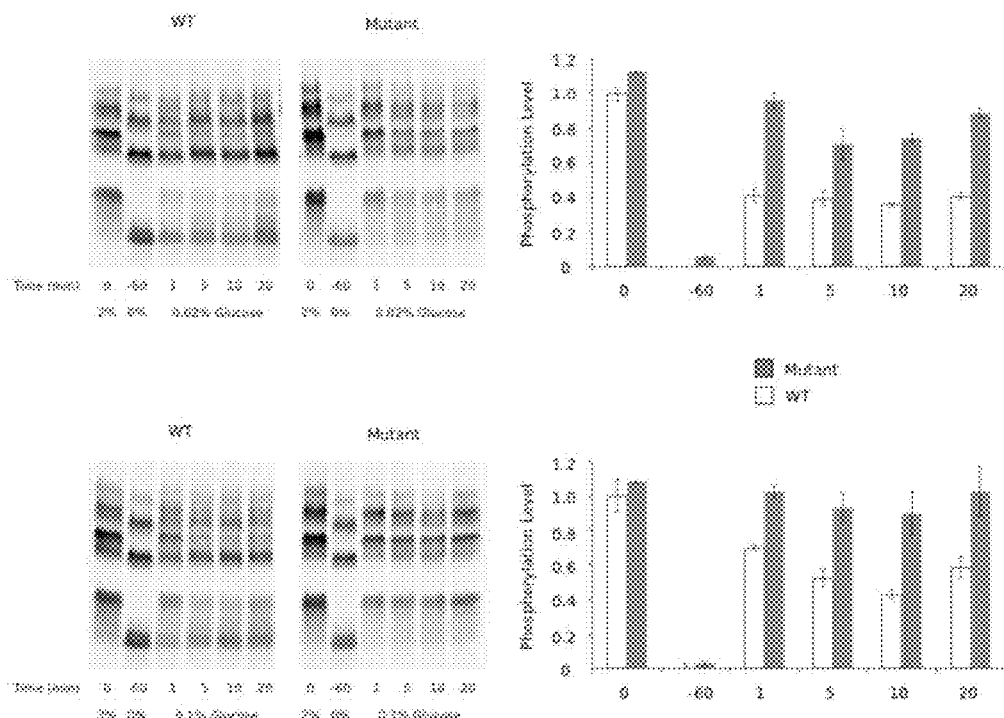
FIG. 11 shows Sch9-HA bandshifts (measuring TORC1 activity) following glucose repletion, indicating that Kog1 foci (Kog1 bodies) formation affects TORC1 signaling.
Figure 12:
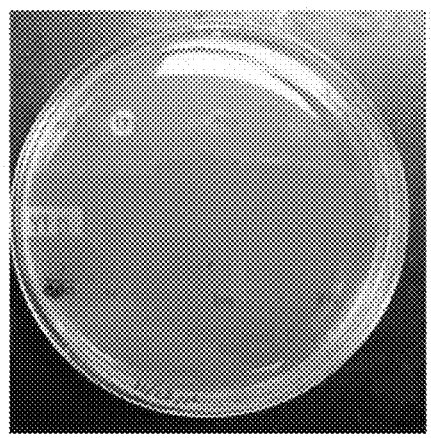
FIG. 12 shows that Kog1 body formation plays a role in cell survival during long-term starvation.
Figure 12:
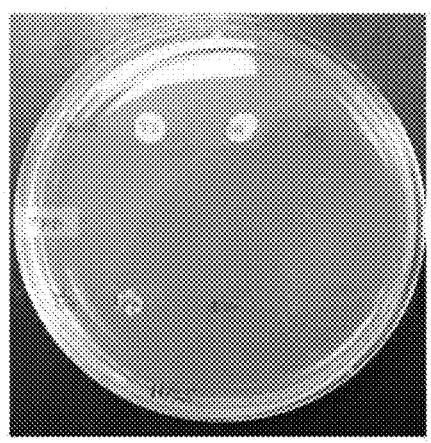

Referring now to FIG. 1-12, the present invention features methods and compositions or agents for treating or preventing diseases or conditions associated with eukaryotic organisms, e.g., fungi, parasites. Without wishing to limit the present invention to any theory or mechanism, the methods of the present invention may feature (a) directly or indirectly triggering/permitting Kog1 aggregation so as to inhibit TOR1 function, (b) directly or indirectly inhibiting Kog1 formation, or (c) another appropriate mechanism. The present invention also features methods for screening for such compositions or agents. The compositions may be used to directly or indirectly trigger/permit Kog1 aggregation to inhibit TORC1 function, or to inhibit Kog1 aggregation rendering the cells more susceptible to stress and starvation. The compositions may be used alone or in combination with other drugs/treatments to fight infection. Without wishing to limit the present invention to any theory or mechanism, it is believed that because the features of the signaling pathway that is the functional basis for these compositions (e.g., Kog1 aggregation determinants) is not present in human cells, it is expected that these compositions may have a low side effect profile and may be safe to use in conjunction with existing treatments.

Non-limiting examples of human diseases caused by eukaryotes include fungal infections (e.g. diseases caused by *Candida albicans, Candida glabrata* and other species) and parasitic diseases (e.g., diseases caused by helminths (parasitic worms), diseases caused by protozoans such as *Plasmodium* (e.g., malaria), diseases caused by *Leishmania* (e.g., leishmaniasis), giardia, etc.).

Non-limiting examples of other formulations that may be used in combination with compositions of the present invention include but are not limited to azoles, echinocandins and polyenes. Azole antifungals include but are not limited to fluconazole, itraconazole, clotrimazole, ketoconazole, posaconazole, voriconazole, butoconazole efinaconazole, luliconazole 1% cream, econazole, miconazole, oxiconazole, sulconazole, terconazole and tioconazole. Echinocandins include but are not limited to Caspofungin, anidulafungin and micafungin. Polyenes include but are not limited to AMB lipid complex, AMB liposomal, AMB cholesteryl sulfate, nystatin, AMB and pimaricin. Allylamines include but are not limited to Amorolfine, Butenafine, Naftifine and Terbinafine. Other antifungals include but are not limited to Griseofulvin, flucytosine, ciprofloxacin 0.3%+dexamethasone 0.1%, sertaconazole nitrate, ciclopirox, Pentamidine isethionate, haloprogin, tolnaftate and undecylenate. Other antifungal therapeutics include but are not limited to chitan synthase inhibitors, and drugs that disrupt mitotic spindle.

The present invention features methods and systems (e.g., compositions) for treating or preventing a disease or a condition associated with a fungus/yeast or a parasite (e.g., in an animal such as a human or other animal). Or the methods and systems may inhibit fungal or parasitic survival or replication in an animal or a plant, or the methods and systems may inhibit fungal or parasitic survival or replication in vitro. In some embodiments, the method comprises administering to an animal, e.g., a human, mouse, rat, fish, etc.), or a plant or other appropriate system, an agent that sensitizes the TORC1 pathway to stress/starvation/treatment via inhibition of Kog1 aggregate formation or inhibits the TORC1 pathway (and growth) by triggering Kog1 aggregate formation.

In some embodiments, the agent comprises a small molecule. Small molecules may include but are not limited to AMPK activators and repressors such as metformin, PT 1, salicylsalicylic acid, Phenformin, AICAR, A-769662, Acadesine, orsomorphin, 1,1-Dimethylbiguanide hydrochloride, BML-275, etc. In some embodiments, the agent binds to Kog1 to inhibit Kog1/TORC1 function. In some embodiments, the agent inhibits Kog1 or Kog1 aggregate formation indirectly. For example, in some embodiments, the agent functions to hyperactive Snf1. In some embodiments, the agent functions to inactivate Snf1.

In some embodiments, the dose of metformin is from 50 mg to 5 g. In some embodiments, the dose of metformin is from 0.1 mg to 10 g. In some embodiments, the dose of metformin is from 1 mg to 100 mg. In some embodiments, the dose of metformin is from 100 mg to 2 g.

In some embodiments, the dose of phenformin is from 50 mg to 5 g. In some embodiments, the dose of phenformin is from 0.1 mg to 10 g. In some embodiments, the dose of phenformin is from 1 mg to 100 mg. In some embodiments, the dose of phenformin is from 100 mg to 2 g.

In some embodiments, the dose of PT1 is from 50 mg to 5 g. In some embodiments, the dose of PT1 is from 0.1 mg to 10 g. In some embodiments, the dose of PT1 is from 1 mg to 100 mg. In some embodiments, the dose of PT1 is from 100 mg to 2 g.

In some embodiments, the dose of salicylsalicylic acid is from 50 mg to 5 g. In some embodiments, the dose of salicylsalicylic acid is from 0.1 mg to 10 g. In some embodiments, the dose of salicylsalicylic acid is from 1 mg to 100 mg. In some embodiments, the dose of salicylsalicylic acid is from 100 mg to 2 g.

In some embodiments, the dose of AICAR is from 50 mg to 5 g. In some embodiments, the dose of AICAR is from 0.1 mg to 10 g. In some embodiments, the dose of AICAR is from 1 mg to 100 mg. In some embodiments, the dose of AICAR is from 100 mg to 2 g.

In some embodiments, the dose of A-769662 is from 50 mg to 5 g. In some embodiments, the dose of A-769662 is from 0.1 mg to 10 g. In some embodiments, the dose of A-769662 is from 1 mg to 100 mg. In some embodiments, the dose of A-769662 is from 100 mg to 2 g.

In some embodiments, the dose of Acadesine is from 50 mg to 5 g. In some embodiments, the dose of Acadesine is from 0.1 mg to 10 g. In some embodiments, the dose of Acadesine is from 1 mg to 100 mg. In some embodiments, the dose of Acadesine is from 100 mg to 2 g.

In some embodiments, the dose of 1,1-Dimethylbiguanide hydrochloride is from 50 mg to 5 g. In some embodiments, the dose of 1,1-Dimethylbiguanide hydrochloride is from 0.1 mg to 10 g. In some embodiments, the dose of 1,1-Dimethylbiguanide hydrochloride is from 1 mg to 100 mg. In some embodiments, the dose of 1,1-Dimethylbiguanide hydrochloride is from 100 mg to 2 g.

In some embodiments, the dose of BML-275 is from 50 mg to 5 g. In some embodiments, the dose of BML-275 is from 0.1 mg to 10 g. In some embodiments, the dose of BML-275 is from 1 mg to 100 mg. In some embodiments, the dose of BML-275 is from 100 mg to 2 g.

In some embodiments, the dose of orsomorphin is from 50 mg to 5 g. In some embodiments, the dose of orsomorphin is from 0.1 mg to 10 g. In some embodiments, the dose of orsomorphin is from 1 mg to 100 mg. In some embodiments, the dose of orsomorphin is from 100 mg to 2 g.

In some embodiments, the agent comprises an antibody or a fragment thereof (e.g., monoclonal, polyclonal antibody/fragment, etc.). The present invention is not limited to the aforementioned agents (e.g., small molecules, drugs, antibodies or antibody fragments).

In some embodiments, the agent comprises a polypeptide adapted to prevent Kog1 aggregate formation. The agent could be a non-antibody peptide that terminally participates in the Kog1 aggregate to block or inhibit aggregate formation (e.g., blocks templating or aggregate extension thus limiting loss of the functional TORC1 complex).

The methods and compositions of the present invention may further comprise the administration of a secondary drug or compound, e.g., an anti-fungal drug, an anti-parasitic drug, or any other appropriate drug or compound. For example, cells that cannot accommodate proper Kog1 aggregation are likely more susceptible to stress, e.g., drug treatments.

The present invention also features methods of screening in vitro for a compound that inhibits Kog1 aggregate formation. In some embodiments, the method comprises introducing a test compound to a first cell system and a second cell system, wherein the first cell system comprising test cells expressing Kog1 labeled with a tag, and the second cell system comprising control cells expressing Kog1 labeled with a tag. The cell systems may then be subjected to a particular stress (e.g., glucose starvation, nitrogen starvation or oxidative stress, etc.). The tags of the cell systems may then be visualized, and the amount of Kog1 aggregates (e.g., the number of foci of the tags (Kog1 bodies), or the size of the foci (signal intensity)) may then be calculated. In some embodiments, if the amount of Kog1 aggregates formed is less in the first cell system than in the second cell system, the compound inhibits Kog1 aggregate formation. If the amount of Kog1 aggregates formed is more in the first cell system than in the second cell system, the compound promotes Kog1 aggregate formation. The tag may comprise a fluorescent protein tag including but not limited to yellow fluorescent protein (YFP), green fluorescent protein (GFP), or red fluorescent protein (RFP). Immunohistochemistry may be used to visualize the Kog1 (e.g., via the tag). In some embodiments, the tag could be an epitope or the native protein and visualized via immunohistochemistry.

Example 1

A 40 year old woman (height of 158 cm, weight of 50 kg) presents to the emergency department exhibiting the following symptoms: difficulty swallowing and sore throat. The physician notes the presence of white plaques on the patient's tongue. The physician diagnoses esophageal candidiasis. The physician administers an oral pharmaceutical containing 200 mg of phenformin, an agent that activates TORC1 aggregate formation. After one day of treatment, the patient shows signs of improvement with the absence of white plaques on the tongue and no difficulty swallowing. By two days of treatment, her sore throat is gone.

Example 2

A 15 year old boy (height of 165 cm, weight of 55 kg) presents to his primary care physician with a red and itchy rash on his forearm. The rash is in a circular pattern. The physician diagnoses the patient with ringworm. The physician administers a dose of a topical pharmaceutical containing 3 g of AICAR, an agent that activates TORC1 aggregate formation. After two days of treatment, the patient shows signs of improvement with the absence of itch on his forearm. By four days of treatment, the rash is gone.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. For example, the present compositions and methods may be effectively used on termites. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of treating a candidiasis infection associated with a *Candida* fungus in a human or animal in need thereof, said method comprising:
   a) identifying a human or animal in need thereof with a candidiasis infection associated with a *Candida* fungus, and
   b) administering an effective amount of a small molecule to the human or animal in need thereof with the candidiasis infection associated with a *Candida* fungus; wherein the small molecule activates Kog1 aggregate formation in the *Candida* fungus, wherein the Kog1 aggregate formation inhibits growth of the *Candida* fungus.

2. The method of claim 1, wherein the small molecule binds Kog1.

3. The method of claim 1, wherein the small molecule comprises metformin, PT 1, salicylsalicylic acid, Phenformin, AICAR, A-769662, Acadesine, orsomorphin, 1,1-Dimethylbiguanide hydrochloride, or BML-275.

4. The method of claim 1, further comprising administering an antifungal drug to the human or animal as a co-treating.

* * * * *

```
                        SEQUENCE LISTING

<160> NUMBER OF SEQ ID NOS: 4

<210> SEQ ID NO 1
<211> LENGTH: 40
<212> TYPE: PRT
<213> ORGANISM: Saccharomyces cerevisiae

<400> SEQUENCE: 1

Leu Gln Ser Arg Lys Ser Ile Ser Leu Gln Ser Ser Gln Gln Gln Leu
1               5                   10                  15

Gln Gln Gln Gln Gln Gln Gln Gln Gln Phe Thr Gly Phe Phe Glu Gln
            20                  25                  30

Asn Leu Thr Ala Phe Glu Leu Trp
        35                  40

<210> SEQ ID NO 2
<211> LENGTH: 40
<212> TYPE: PRT
<213> ORGANISM: Saccharomyces cerevisiae

<400> SEQUENCE: 2

Gln Leu His Ser Gln Leu Gln His Leu Gln Asn Gln Ser His Leu Gln
1               5                   10                  15

Gln Gln Gln Ser Gln Gln Gln Gln Gln His Leu Glu Gln Gln Gln Met
            20                  25                  30

Lys Ile Glu Lys Gln Ile Arg His
        35                  40

<210> SEQ ID NO 3
<211> LENGTH: 40
<212> TYPE: PRT
<213> ORGANISM: Artificial Sequence
<220> FEATURE:
<223> OTHER INFORMATION: Some Glutamines (residues 13-15 and 17-25) of
      SEQ ID NO: 1 were changed to Alanine

<400> SEQUENCE: 3

Leu Gln Ser Arg Lys Ser Ile Ser Leu Gln Ser Ser Ala Ala Ala Leu
1               5                   10                  15

Ala Ala Ala Ala Ala Ala Ala Ala Ala Phe Thr Gly Phe Phe Glu Gln
            20                  25                  30

Asn Leu Thr Ala Phe Glu Leu Trp
        35                  40

<210> SEQ ID NO 4
```

```
<211> LENGTH: 40
<212> TYPE: PRT
<213> ORGANISM: Artificial Sequence
<220> FEATURE:
<223> OTHER INFORMATION: Some glutamines (Residues 16-19 and 21-25) of
      SEQ ID NO:2 were changed to alanine.

<400> SEQUENCE: 4

Gln Leu His Ser Gln Leu Gln His Leu Gln Asn Gln Ser His Leu Ala
1               5                   10                  15

Ala Ala Ala Ser Ala Ala Ala Ala Gln His Leu Glu Gln Gln Gln Met
            20                  25                  30

Lys Ile Glu Lys Gln Ile Arg His
        35                  40
```